United States Patent
Li et al.

(10) Patent No.: US 12,114,565 B2
(45) Date of Patent: Oct. 8, 2024

(54) ORGANIC ELECTROLUMINESCENT MATERIAL AND APPLICATION THEREOF

(71) Applicant: GUANGDONG AGLAIA OPTOELECTRONIC MATERIALS CO., LTD, Guangdong (CN)

(72) Inventors: Huiyang Li, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 763 days.

(21) Appl. No.: 17/298,003

(22) PCT Filed: Nov. 2, 2019

(86) PCT No.: PCT/CN2019/115179
§ 371 (c)(1),
(2) Date: May 27, 2021

(87) PCT Pub. No.: WO2020/125240
PCT Pub. Date: Jun. 25, 2020

(65) Prior Publication Data
US 2022/0115599 A1    Apr. 14, 2022

(30) Foreign Application Priority Data

Dec. 19, 2018   (CN) .......................... 201811566947.3

(51) Int. Cl.
| | |
|---|---|
| *H01L 51/00* | (2006.01) |
| *C07D 491/153* | (2006.01) |
| *C09K 11/06* | (2006.01) |
| *H10K 85/60* | (2023.01) |
| *H10K 50/11* | (2023.01) |
| *H10K 50/16* | (2023.01) |
| *H10K 50/17* | (2023.01) |
| *H10K 102/00* | (2023.01) |

(52) U.S. Cl.
CPC ....... *H10K 85/657* (2023.02); *C07D 491/153* (2013.01); *C09K 11/06* (2013.01); *C09K 2211/1018* (2013.01); *H10K 50/11* (2023.02); *H10K 50/16* (2023.02); *H10K 50/17* (2023.02); *H10K 2102/351* (2023.02)

(58) Field of Classification Search
CPC ............ H01L 51/0071; H01L 51/5088; C07D 491/153; C09K 2211/1018; C09K 11/06
See application file for complete search history.

(56) References Cited

U.S. PATENT DOCUMENTS

| | | | |
|---|---|---|---|
| 2009/0054454 A1 | 2/2009 | Venkatesan et al. | |
| 2009/0315022 A1 | 12/2009 | Morishita et al. | |
| 2014/0246663 A1 | 9/2014 | Kambe et al. | |

FOREIGN PATENT DOCUMENTS

| | | | | |
|---|---|---|---|---|
| CN | 101874021 A | * | 10/2010 | ........... C07D 221/18 |
| WO | WO-2007149478 A2 | * | 12/2007 | ......... A61K 49/0021 |

* cited by examiner

*Primary Examiner* — Robert D Harlan
(74) *Attorney, Agent, or Firm* — Maschoff Brennan

(57) ABSTRACT

The invention provides an organic electroluminescent material and application thereof. The organic electroluminescent material of the invention contains pyrazine and cyano groups, has the structure of Formula (I). The organic electroluminescent device manufactured by doping with the compound of the invention can significantly improve the power efficiency, and can reduce the turn-on voltage.

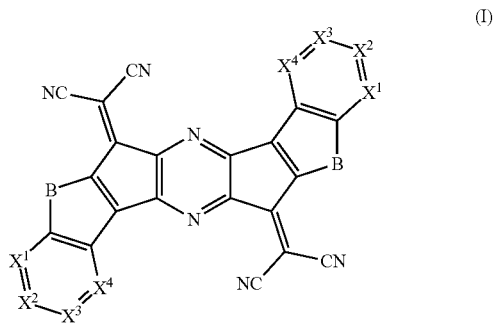

20 Claims, 1 Drawing Sheet

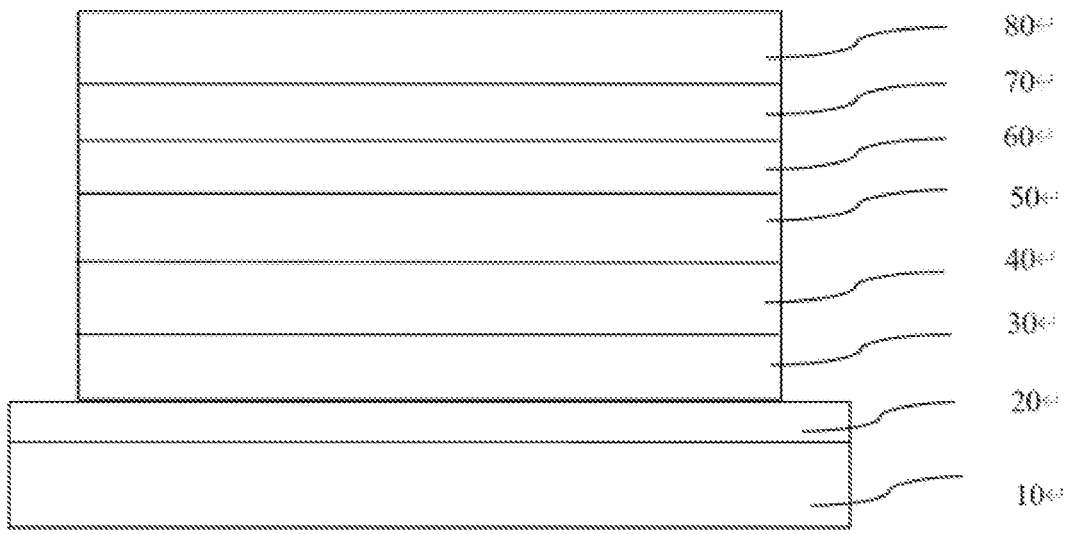

ORGANIC ELECTROLUMINESCENT MATERIAL AND APPLICATION THEREOF

FIELD OF THE INVENTION

The invention relates to the field of organic electroluminescent materials, in particular to an electroluminescent material containing pyrazine and cyano groups and application thereof.

BACKGROUND

In recent years, organic light-emitting diodes (OLED), as a kind of lighting and display technology with huge application prospects, have received extensive attention from academia and industry. OLED devices have characteristics such as self-luminescence, wide viewing angle, short response time and ability to prepare flexible device, so they become a strong competitor of next-generation display and lighting technology. However, OLEDs still have problems such as low efficiency and short life span, which need to be further studied.

Since Forrest et al. reported on electro-phosphorescent devices (PHOLED) in 1998, organic electroluminescent devices have achieved industrial applications. Its advantage lies in breaking through the limit that the organic electroluminescence quantum efficiency is less than 25%, and increasing the quantum yield up to 100%. High-efficiency PHOLED devices usually have a multilayer structure, including a cathode, an anode, and an organic layer. The organic layer is one or more of a hole injection layer, a hole transport layer, a light-emitting layer, a hole blocking layer, an electron injection layer and an electron transport layer. The organic layer does not have to contain all the layers, and part of the organic layer can be added or reduced according to actual conditions. The advantage is that the process of carrier injection, transmission and recombination can be conveniently adjusted to improve the efficiency of carrier transmission and recombination.

An important aspect of optimizing the performance of organic electroluminescent devices is to adjust the charge injection between adjacent organic functional layers in order to promote the formation of excitons, thereby improving luminous efficiency. TCNQF4 is often used as a hole injection layer, which can effectively promote hole injection and reduce driving voltage, but due to its small molecular weight and good volatility, it is easy to contaminate the evaporation apparatus and devices during the vapor deposition process.

SUMMARY

The purpose of the present invention is to provide an organic electroluminescent material containing pyrazine and cyano groups, which can effectively reduce the voltage of the device while increasing the efficiency.

An organic electroluminescent material has a compound with the structure of Formula (I):

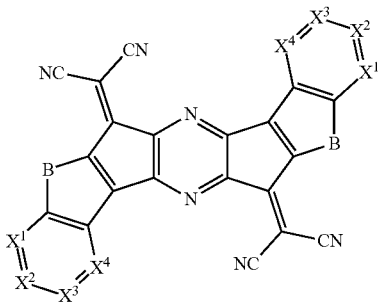

(I)

Where, B is selected from O, S and $NR^1$, and $R^1$ is selected from a C1-C6 alkyl group, a C3-C40 heteroaryl group and a C6-C40 aryl group.

$X_1$-$X_4$ are independently selected from N and $CR^2$, and $R^2$ is selected from a hydrogen atom, a deuterium atom, a C1-C6 alkyl group, a C3-C40 heteroaryl group and a C6-C40 aromatic group.

Preferably, B is selected from O, S and $NR^1$, and $R^1$ is selected from a C1-C6 alkyl group, a C3-C9 heteroaryl group and a C6-C14 aryl group.

$X_1$-$X_4$ are independently selected from N and $CR^2$, and $R^2$ is selected from a hydrogen atom, a deuterium atom, a C1-C6 alkyl group, a C3-C9 heteroaryl group and a C6-C14 aromatic group.

Preferably, B is selected from O, S and $NR^1$, and $R^1$ is selected from a methyl group, a phenyl group, a tolyl group, a naphthyl group and a pyridyl group.

$X_1$-$X_4$ are independently selected from N and CH.

More preferably, B is selected from O, S and $NR^1$, and $R^1$ is selected from a methyl group, a phenyl group and a pyridyl group.

$X_1$-$X_4$ are independently selected from N and CH.

More preferably, B is selected from O, S and $NR^1$, and $R^1$ is selected from a methyl group, a phenyl group, and a pyridyl group.

Among $X_1$-$X_4$, 0-2 are N, and the rest are CH.

Further preferably, the luminescent material represented by Formula (I) of the invention is the following Compounds 1-18, but not limited to the listed structures:

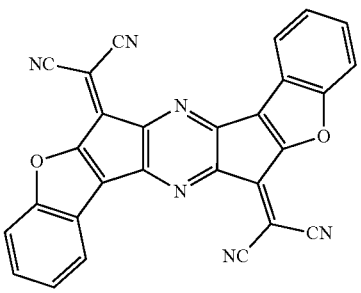

1

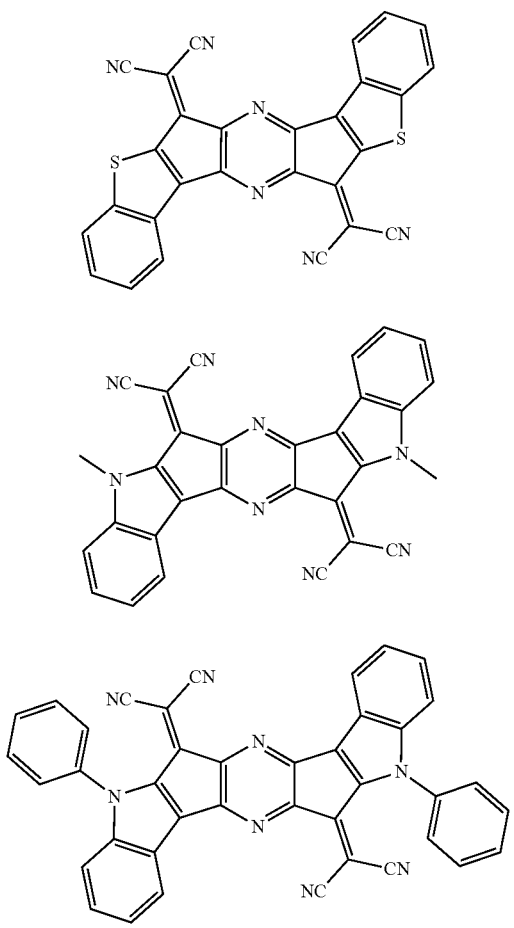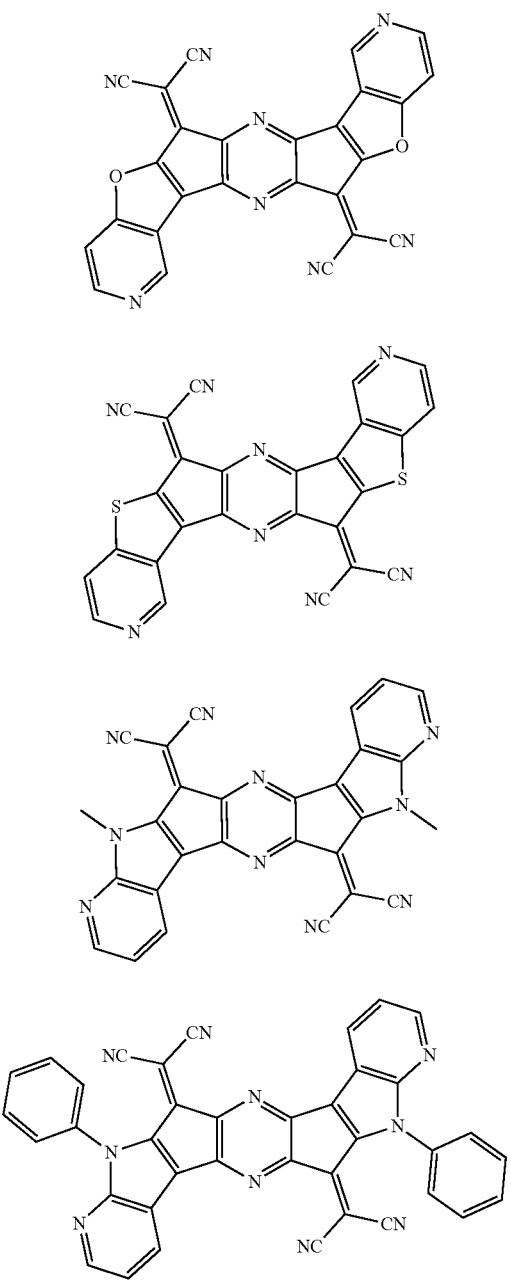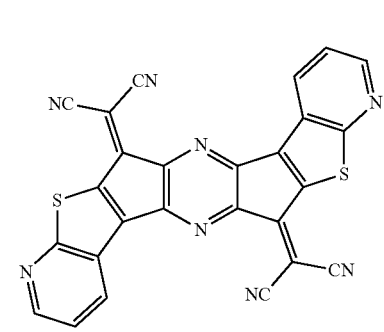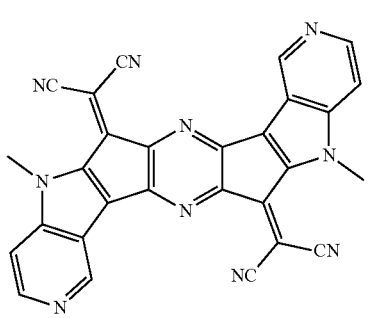

12

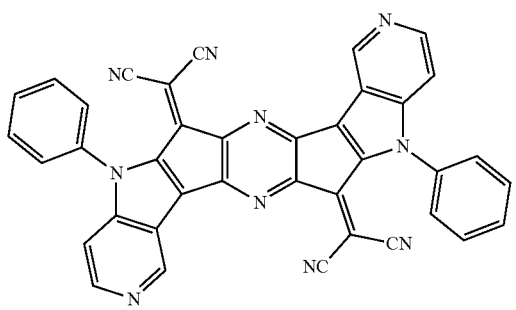

13

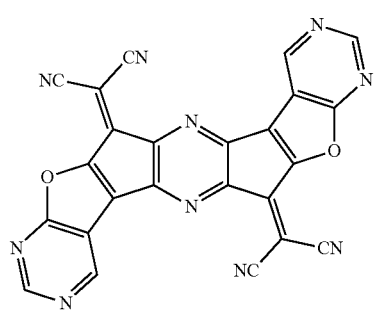

14

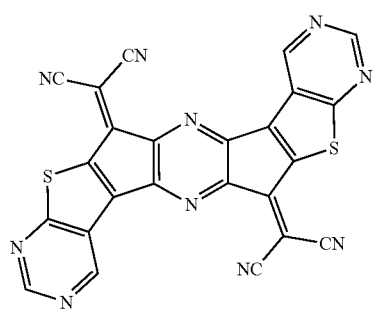

15

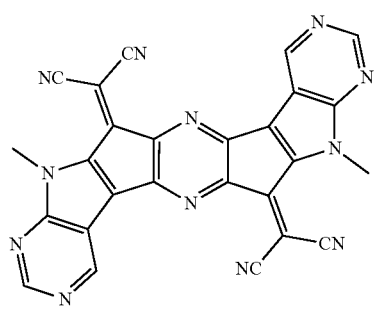

16

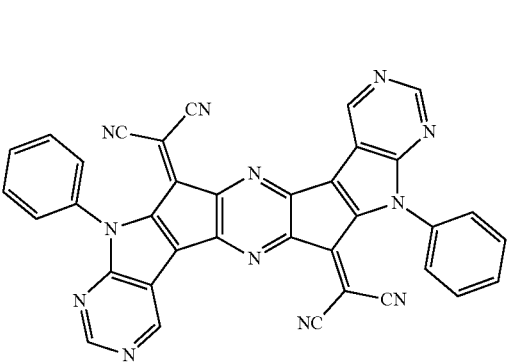

17

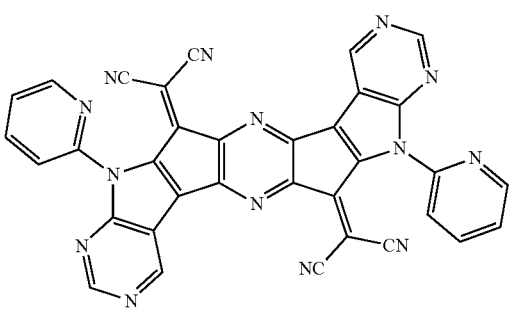

18

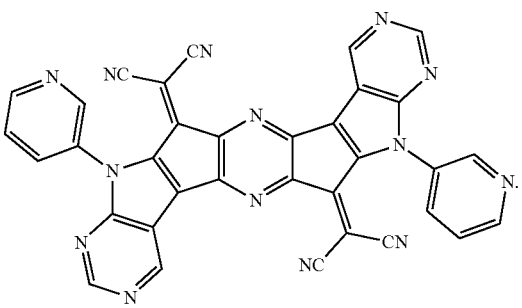

The above-mentioned compounds are applied to organic electroluminescent devices, mechanoluminescent devices, organic field effect transistors, organic solar cells and chemical sensors.

The present does not specifically limit the preparation method of the compound presented by Formula (I). the compound

1

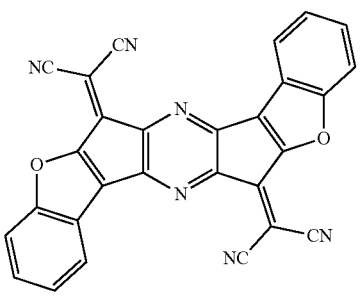

is typically but unrestrictedly taken as an illustrative example. The synthesis and preparation methods are as follows:

The synthesis route is as follows:

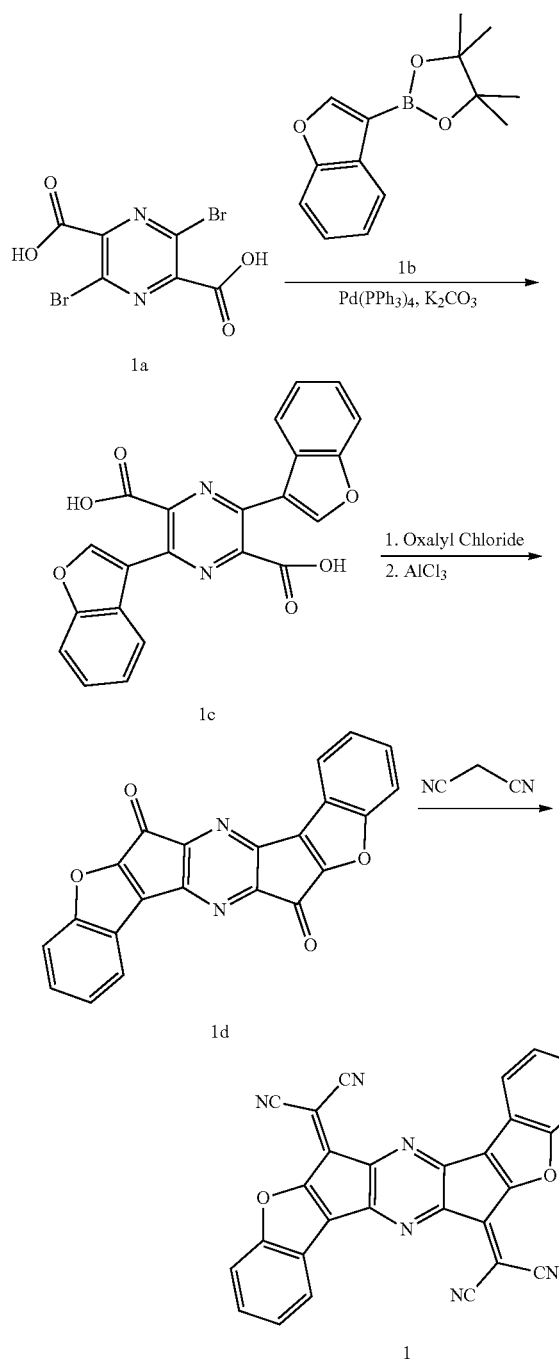

The synthesis method is as follows:

The Reactant 1a (1eq) reacts with benzofuran-2-boronic acid ester 1b (2.1eq) by pd-catalyzed coupling reaction under a nitrogen atmosphere to obtain the Intermediate 1c. The Intermediate 1d is obtained from the Intermediate 1c through intramolecular ring-closure reaction, and then the Compound 1 is obtained through condensation reaction.

A skilled person in the art should understand that the above preparation method is only an exemplary example. A skilled person in the art can obtain other compounds of the invention by improving technology hereof.

The organic electroluminescent device according to the invention includes a cathode, an anode, and an organic layer. The organic layer is one or more of a hole injection layer, a hole transport layer, a light-emitting layer, a hole-blocking layer, an electron injection layer, and an electron transport layer, each of which need not be incorporated in the organic layer.

At least one of the hole injection layer, hole transport layer, hole-blocking layer, light-emitting layer and/or electron transport layer contains the compound represented by Formula (I).

Preferably, the layer where the compound represented by Formula (1) is located is a light-emitting layer or an electron transport layer.

The total thickness of the device's organic layer according to the invention is 1-1000 nm, preferably 1-500 nm, and more preferably 5-300 nm.

The organic layer can be formed into a thin film by vapor deposition or solution method.

The experimental results show that the organic electroluminescent material of the present invention can effectively reduce the voltage of the device, as well as improve the photoelectric efficiency of the device, with the potential to be applied to organic electroluminescent devices.

BRIEF DESCRIPTION OF THE DRAWINGS

FIG. 1 is a structural diagram of the organic electroluminescent device according to invention.

10—glass substrate, 20—anode, 30—hole injection layer, 40—hole transport layer, 50—light-emitting layer, 60—electron transport layer, 70—electron injection layer, 80—cathode.

DETAILED DESCRIPTION OF THE PREFERRED EMBODIMENTS

The invention will be further described in detail with reference to the examples as follows.

Example 1

Synthetizing Compound 1

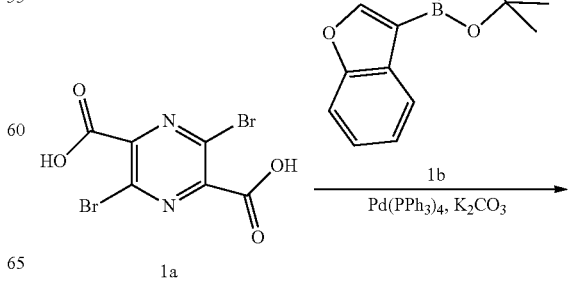

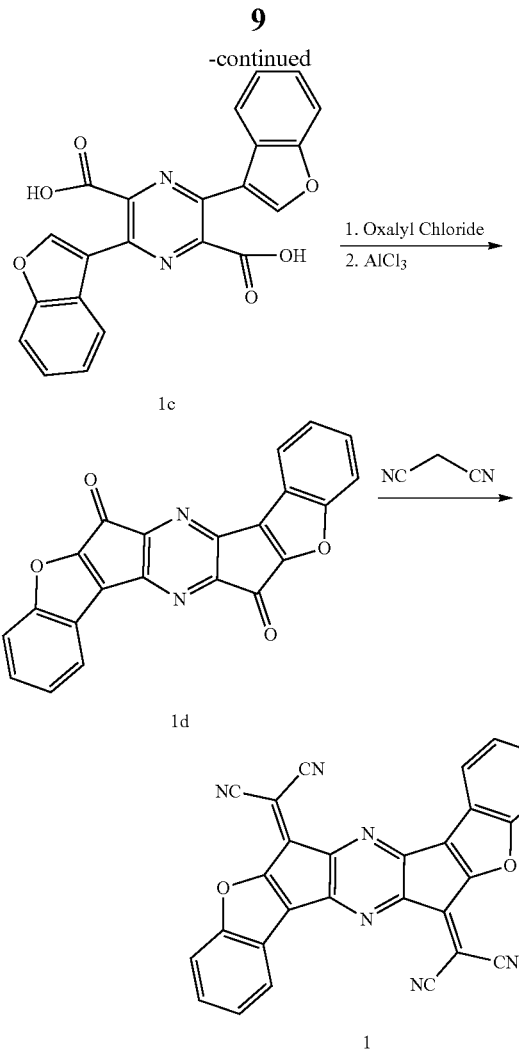

Synthetizing Intermediate 1c

The Compound 1a (3.3 g, 10.0 mmol) (synthesized by reference to WO2007/149478), benzofuran-2-borate 1b (5.2 g, 21.0 mmol) (synthesized by reference to US2009/54454), Pd(PPh$_3$)$_4$ (0.58 g, 0.5 mmol), K$_2$CO$_3$ (6.9 g, 50.0 mmol), tetrahydrofuran (30 mL) and water (5 mL) are sequentially added to the Schlenk tube under a nitrogen atmosphere, heated to 80° C. and react for 24 hours. After cooling to room temperature, the above reaction solution is added to water, and its pH is adjusted to neutrality with hydrochloric acid, then a light yellow solid is separated out. The solid is recrystallized with n-hexane and methanol to obtain the Intermediate 1c (2.5 g, the yield is 62%).

Synthetizing Intermediate 1d

The Compound 1c (1.5 g, 3.8 mmol) is dissolved in oxalyl chloride (20 mL), which DMF (0.5 mL) is added to dropwise and heated to reflux for 6 hours under a nitrogen atmosphere. The oxalyl chloride is removed under reduced pressure, then the residue is dissolved in dichloromethane which is cooled to 0° C., to which aluminum trichloride (20.0 g, 15 mmol) is added, then the reaction solution is gradually heated to room temperature and stirred for 24 hours. Finally, the reaction solution is added to hydrochloric acid (2 M, 20 mL), stirred for 1 hour, and filtered to obtain a purple solid (1.1 g, the yield is 80%).

Synthetizing Compound 1

The Compound 1d (1.0 g, 3.8 mmol) and malononitrile (3.3 g, 50 mmol) are dissolved in pyridine (50 mL) and stirred at room temperature overnight under a nitrogen atmosphere. A purple solid is obtained by filtration and recrystallized with methanol to obtain the Compound 1 (0.6 g, the yield is 34%). ESI-MS (m/z): 461.1 (M+1).

Example 2

The organic light-emitting material according to the invention is used to prepare an electroluminescent device, the structure of which is shown in FIG. 1.

First, washing the transparent conductive ITO glass substrate 10 (with an anode 20 on it) sequentially by detergent solution, deionized water, ethanol, acetone, and deionized water, and then treating it with oxygen plasma for 30 seconds.

Then, evaporatively depositing a 10 nm hole injection layer 30 on the ITO. The hole injection layer is composed of compound 1 (3%) and HT1 (97%) by co-doping.

Then, evaporatively depositing HT1 to form a 40 nm hole transport layer 40.

Then, evaporatively depositing a 30 nm thick light-emitting layer 50 on the hole transport layer. The light-emitting layer is composed of Ir(PPy)$_3$ (10%) and CBP (90%) by co-doping.

Then, evaporatively depositing a 50 nm thick AlQ$_3$ on the light-emitting layer as the electron transport layer 60.

Finally, evaporatively depositing a 1 nm thick LiF as the electron injection layer 70 and a 100 nm thick Al as the device cathode 80.

COMPARATIVE EXAMPLE

A 10 nm thick HT1 is evaporatively deposited as the hole injection layer, and the remaining layers are the same as those described in Example 2. The organic light-emitting device is manufactured according to the same method.

The structure presented in the device is as bellows.

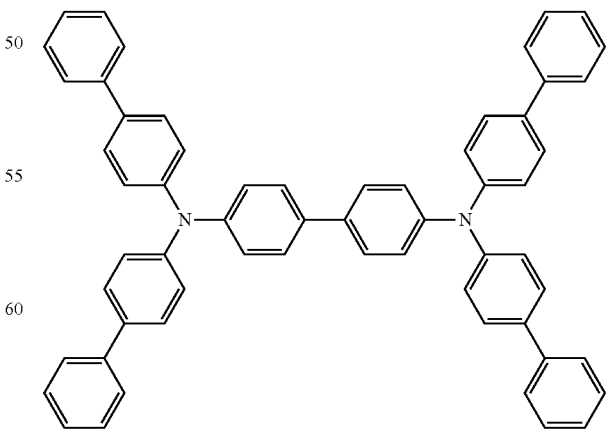

HT1

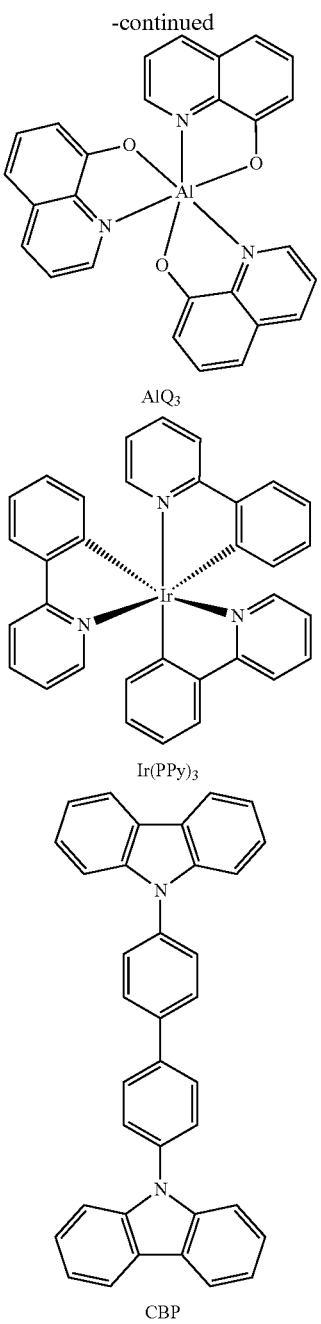

AlQ₃

Ir(PPy)₃

CBP

The efficiency of the organic electroluminescent devices in Example 2 and Comparative Example at a current density of 10 mA/cm² is as follows:

| Light emitting devices | Hole injection layer | Maximum power efficiency (lm/W) | Turn on voltage (V) | Luminous color |
|---|---|---|---|---|
| Example 2 | Compound 1(3%)/ HT1(97%) | 51.2 | 3.2 | green |
| Comparative Example | HT1 | 37.8 | 3.9 | green |

Under the same conditions, the power efficiency of the organic electroluminescent device manufactured by doping with the compound of the invention is significantly better than that of the Comparative Example, and the turn-on voltage can be reduced, which is of great significance for optimizing the performance of organic optoelectronic devices.

The various embodiments described above are only examples, and are not intended to limit the scope of the invention. Without departing from the essence of the invention, various materials and structures in the invention can be replaced by other materials and structures. It should be understood that a skilled person in the art can make many modifications and changes according to the idea of the invention without creative effort. Therefore, the technical solutions that can be obtained by the skilled person through analysis, ratiocination or partial research on the basis of the prior art should be within the protection scope defined by the claims.

What is claimed is:

1. An organic electroluminescent material having a chemical structure of Formula (I),

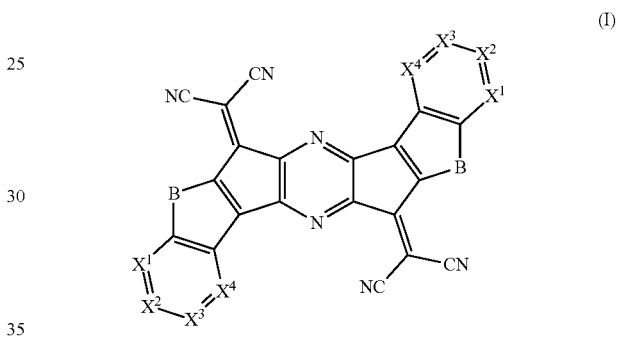

where:
B is selected from O, S or NR¹,
R¹ is selected from a C1-C6 alkyl group, a C3-C40 heteroaryl group or a C6-C40 aryl group,
$X_1$-$X_4$ are independently selected from N or CR², and
R² is selected from a hydrogen atom, a deuterium atom, a C1-C6 alkyl group, a C3-C40 heteroaryl group or a C6-C40 aromatic group.

2. The organic electroluminescent material according to claim 1, wherein:
B is selected from O, S or NR¹,
R¹ is selected from a C1-C6 alkyl group, a C3-C9 heteroaryl group or a C6-C14 aryl group,
$X_1$-$X_4$ are independently selected from N or CR², and
R² is selected from a hydrogen atom, a deuterium atom, a C1-C6 alkyl group, a C3-C9 heteroaryl group or a C6-C14 aromatic group.

3. The organic electroluminescent material according to claim 2, wherein:
B is selected from O, S or NR¹,
R¹ is selected from a methyl group, a phenyl group, a tolyl group, a naphthyl group or a pyridyl group, and
$X_1$-$X_4$ are independently selected from N or CH.

4. The organic electroluminescent material according to claim 3, wherein:
B is selected from O, S or NR¹,
R¹ is selected from a methyl group, a phenyl group or a pyridyl group, and
$X_1$-$X_4$ are independently selected from N or CH.

5. The organic electroluminescent material according to claim 4, wherein:

B is selected from O, S or NR$^1$, and
R$^1$ is selected from a methyl group, a phenyl group, or a pyridyl group, among $X_1$-$X_4$, there are 0-2 N, and the rest are CH.
6. An organic electroluminescent material according to claim 1, comprising the following compounds:
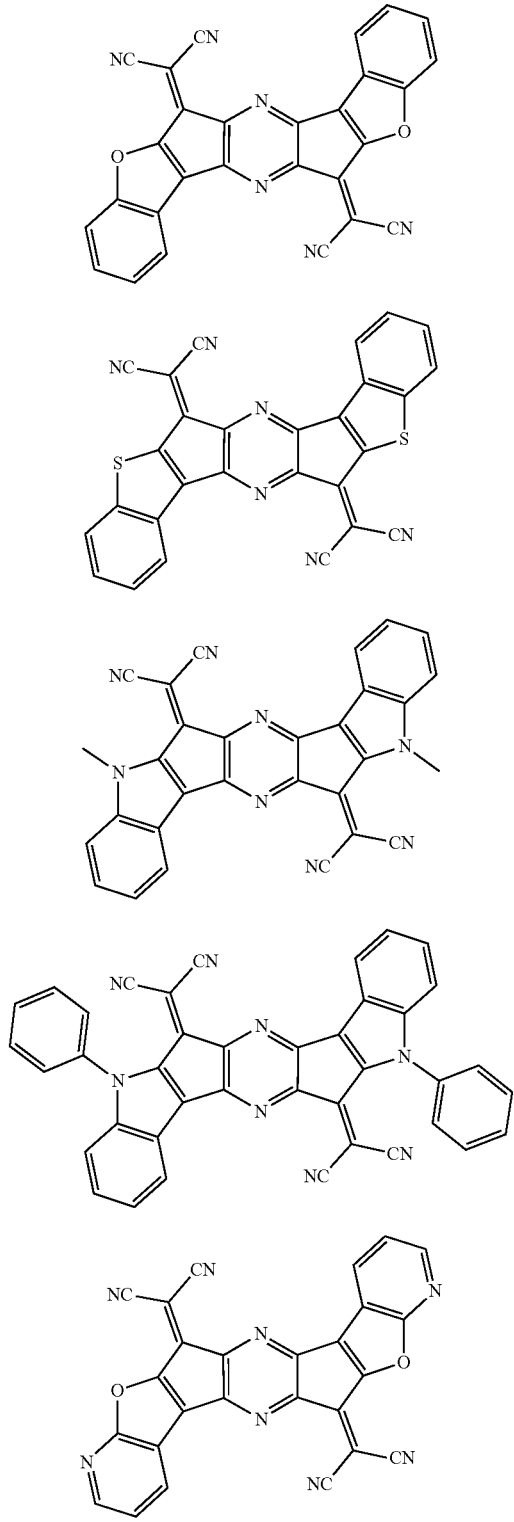
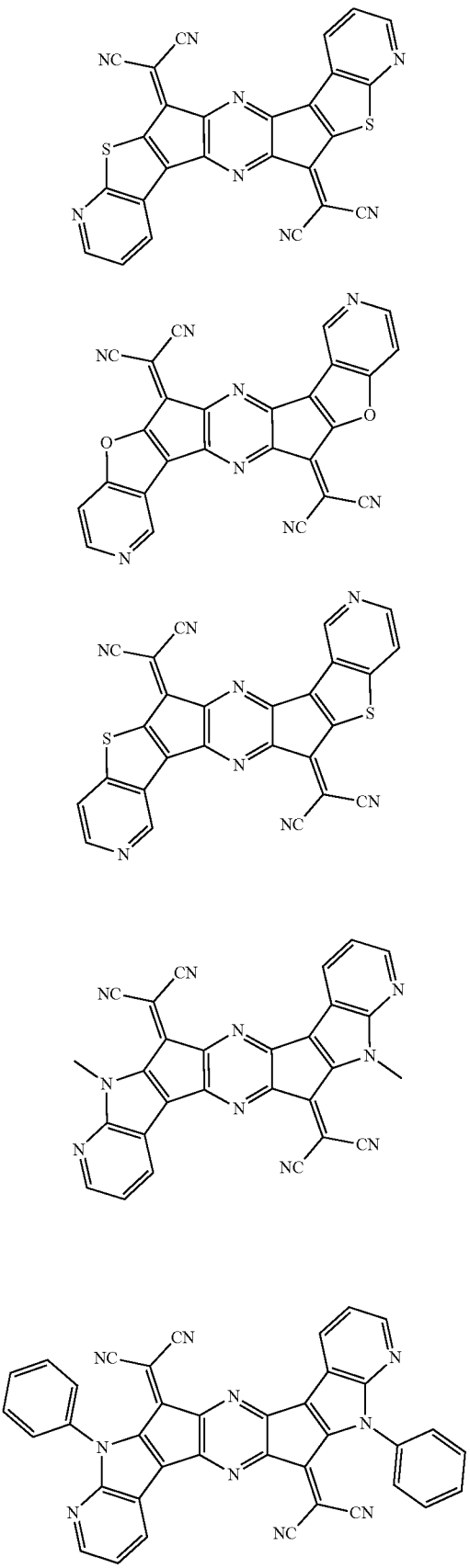

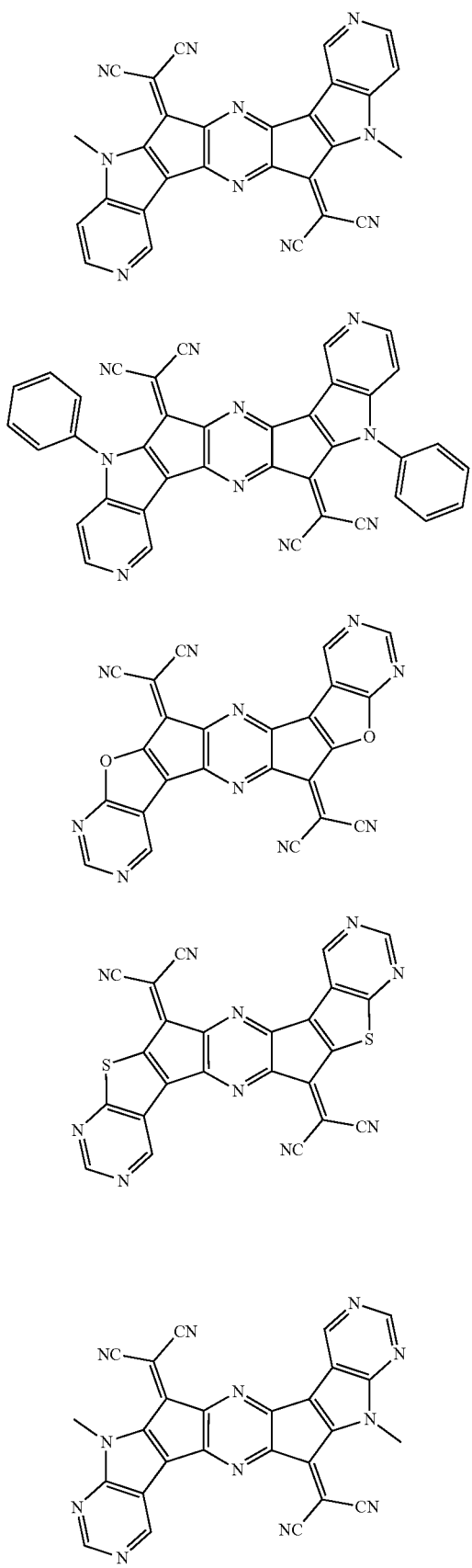

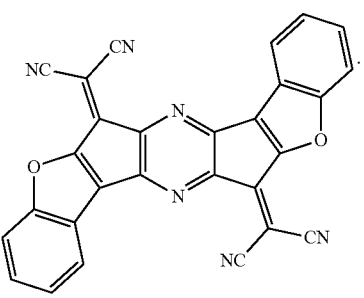

7. An organic electroluminescent material according to claim 6, (Original) comprising the following compounds:

8. An organic electroluminescence device comprising:
an anode,
a cathode, and
an organic layer including one or more of a light-emitting layer, a hole injection layer, a hole transport layer, an electron injection layer, and an electron transport layer, said organic layer containing said organic electroluminescent material according to claim 1.

9. The organic electroluminescence device according to claim 8, wherein:

the layer containing said organic electroluminescent material is a hole injection layer or an electron transport layer, and said organic electroluminescent material is used alone, or in combination with other compounds.

10. The organic electroluminescence device according to claim 8, wherein:

the total thickness of said organic layer is 1-1000 nm, and said organic layer is formed into a thin film by vapor deposition or solution method.

11. An organic electroluminescence device comprising:

an anode, a cathode, and an organic layer including one or more of a light-emitting layer, a hole injection layer, a hole transport layer, an electron injection layer, and an electron transport layer, said organic layer containing said organic electroluminescent material according to claim 2.

12. The organic electroluminescence device according to claim 11, wherein:

the layer containing said organic electroluminescent material is a hole injection layer or an electron transport layer, and said organic electroluminescent material is used alone, or in combination with other compounds.

13. The organic electroluminescence device according to claim 11, wherein:

the total thickness of said organic layer is 1-1000 nm, and said organic layer is formed into a thin film by vapor deposition or solution method.

14. An organic electroluminescence device comprising:

an anode, a cathode, and an organic layer including one or more of a light-emitting layer, a hole injection layer, a hole transport layer, an electron injection layer, and an electron transport layer, said organic layer containing said organic electroluminescent material according to claim 3.

15. The organic electroluminescence device according to claim 14, wherein:

the layer containing said organic electroluminescent material is a hole injection layer or an electron transport layer, and said organic electroluminescent material is used alone, or in combination with other compounds.

16. The organic electroluminescence device according to claim 14, wherein:

the total thickness of said organic layer is 1-1000 nm, and said organic layer is formed into a thin film by vapor deposition or solution method.

17. An organic electroluminescence device comprising:

an anode, a cathode, and an organic layer including one or more of a light-emitting layer, a hole injection layer, a hole transport layer, an electron injection layer, and an electron transport layer, said organic layer containing said organic electroluminescent material according to claim 4.

18. An organic electroluminescence device comprising:

an anode, a cathode, and an organic layer including one or more of a light-emitting layer, a hole injection layer, a hole transport layer, an electron injection layer, and an electron transport layer, said organic layer containing said organic electroluminescent material according to claim 5.

19. An organic electroluminescence device comprising:

an anode, a cathode, and an organic layer including one or more of a light-emitting layer, a hole injection layer, a hole transport layer, an electron injection layer, and an electron transport layer, said organic layer containing said organic electroluminescent material according to claim 6.

20. An organic electroluminescence device comprising:

an anode, a cathode, and an organic layer including one or more of a light-emitting layer, a hole injection layer, a hole transport layer, an electron injection layer, and an electron transport layer, said organic layer containing said organic electroluminescent material according to claim 7.

* * * * *